(12) United States Patent
Yasuda et al.

(10) Patent No.: US 9,109,197 B2
(45) Date of Patent: Aug. 18, 2015

(54) DEVICE FOR CONCENTRATING AND SEPARATING CELLS

(75) Inventors: Kenji Yasuda, Tokyo (JP); Masahito Hayashi, Kawasaki (JP); Akihiro Hattori, Tokyo (JP)

(73) Assignees: Kanagawa Academy of Science and Technology, Kanagawa (JP); National University Corporation Tokyo Medical and Dental University, Tokyo (JP)

( * ) Notice: Subject to any disclaimer, the term of this patent is extended or adjusted under 35 U.S.C. 154(b) by 327 days.

(21) Appl. No.: 13/138,785

(22) PCT Filed: Mar. 31, 2010

(86) PCT No.: PCT/JP2010/055793
§ 371 (c)(1),
(2), (4) Date: Dec. 19, 2011

(87) PCT Pub. No.: WO2010/113994
PCT Pub. Date: Oct. 7, 2010

(65) Prior Publication Data
US 2012/0088295 A1    Apr. 12, 2012

(30) Foreign Application Priority Data

Mar. 31, 2009  (JP) ................... 2009-086076
Feb. 24, 2010  (JP) ................... 2010-039371

(51) Int. Cl.
*C12M 1/34*    (2006.01)
*C12M 3/00*    (2006.01)
*C12M 1/00*    (2006.01)

(52) U.S. Cl.
CPC ................... *C12M 47/04* (2013.01)

(58) Field of Classification Search
CPC ....................................... C12M 47/04
USPC ............................ 435/283.1–309.4
See application file for complete search history.

(56) References Cited

U.S. PATENT DOCUMENTS

2006/0073076 A1    4/2006 Ichiki et al.
2006/0139638 A1*   6/2006 Muller et al. ............. 356/342
(Continued)

FOREIGN PATENT DOCUMENTS

JP    3004720 B2    11/1999
JP    2003-107099 A    4/2003
(Continued)

OTHER PUBLICATIONS

Choi et al., "Microfluidic system for dielectrophoretic separation based on a trapezoidal electrode array," Lab Chip, 2005, 1161-1167.
Fiedler et al., "Dielectrophoretic Sorting of Particles and Cells in a Microsystem," Analytical Chemistry, 1998, 70:1909-1915.
(Continued)

*Primary Examiner* — Nathan Bowers
*Assistant Examiner* — Lydia Edwards
(74) *Attorney, Agent, or Firm* — Foley & Lardner LLP

(57) ABSTRACT

Provided is a device for concentrating and separating cells, which has a function for continuously concentrating cells; a function for then continuously arranging the concentrated cells in predetermined regions of a flow path; a function for simultaneously identifying shape and fluorescent emission in one-cell units on the basis of cell concentration and purification images, which serve to continuously separate and purify cells that have different properties in that they are either attracted to or repelled by an induction electrophoresis force of a predetermined frequency; and a function for identifying cells on the basis of this shape and fluorescent emission information and thereby separating and purifying the cells.

22 Claims, 13 Drawing Sheets

(56) References Cited

U.S. PATENT DOCUMENTS

| | | |
|---|---|---|
| 2006/0141618 A1 | 6/2006 | Yasuda et al. |
| 2006/0152708 A1* | 7/2006 | Muller et al. .................. 356/73 |
| 2006/0177815 A1* | 8/2006 | Soh et al. ......................... 435/4 |
| 2008/0283401 A1* | 11/2008 | Peach ............................ 204/547 |

FOREIGN PATENT DOCUMENTS

| | | |
|---|---|---|
| JP | 2004-085323 A | 3/2004 |
| JP | 2009-262107 A | 11/2009 |
| WO | WO 97/27933 A1 | 8/1997 |
| WO | WO 98/04355 A1 | 2/1998 |
| WO | WO 92/07657 B2 | 5/1999 |
| WO | WO 99/62622 A1 | 12/1999 |
| WO | WO 2004/019033 A1 | 3/2004 |
| WO | WO 2004/070361 A1 | 8/2004 |
| WO | WO 2004/070362 A1 | 8/2004 |
| WO | WO 2004/101731 A1 | 11/2004 |

OTHER PUBLICATIONS

Kamarck et al., "Fluorescence-Activated Cell Sorting of Hybrid and Transfected Cells," Methods in Enzymology, 1987, 151:150-165.

Mueller et al., "A 3-D microelectrode system for handling and caging single cells and particles," Biosensors & Bioelectronics, 1999, 14:247-256.

Wolff et al., "Rare event cell sorting in a microfluidic system for application in prenatal diagnosis," Micro Total Analysis, 1998, 98:77-80.

Yasuda, Kenji, "Separation and purification of single cells using on-chip cell sorter," Biomaterials—Seibutsu Zairyo, 2003, 21(2):127-132.

Yasuda, Kenji,"Nano-biology: Nanotech de Bio o Kaeru," Tan'itsu Sosa • Seisei Gijutsu. Saibo Kogaku, 2006, 25(8):884-888.

Zhang et al., "Dielectrophoresis for manipulation of micro/nano particles in microfluidic systems," Analytical and Bioanalytical Chemistry, 2010, 396(1):401-420.

* cited by examiner

DEVICE FOR CONCENTRATING AND SEPARATING CELLS

CROSS-REFERENCE TO RELATED APPLICATIONS

This application is a National Stage application of PCT/JP2010/055793, filed Mar. 31, 2010, which claims priority from Japanese applications JP 2009-086706, filed Mar. 31, 2009, and JP 2010-039371, filed Feb. 24, 2010.

TECHNICAL FIELD

The present invention relates to a device for concentrating and separating cells.

BACKGROUND ART

A biological tissue of a multicellular organism maintains a harmonious function as a whole by various cells taking on different roles. Once some cells become cancerous (hereinafter collectively referred to as a cancer, including a tumor), the cells grow into neoplasm different from its peripheral region. However, the cancerous region and a normal tissue region far away from the cancerous region are not necessarily distinguished by a certain borderline, and the peripheral region surrounding the cancerous region is affected to some extent. Therefore, in order to analyze a function of an organ tissue, it is necessary to separate a small number of cells present in a small region as easily as possible with minimal loss for a short time.

In the field of regeneration medicine, an attempt is being made to separate an organ stem cell from a tissue, reculture the stem cell, and induce the differentiation of the stem cell to regenerate a target tissue, and furthermore an organ.

To identify or separate cells, it is necessary to distinguish the cells according to a certain index. Common methods of distinguishing cells include the following:

1) Morphological cell classification based on visual observation: Examples include an examination for bladder cancer, urethral cancer and the like by an examination for atypical cells present in urine, and a cancer screening by classification of atypical cells in blood or cytological diagnosis in a tissue.
2) Cell classification based on cell surface antigen (marker) staining by a fluorescent antibody method: This is to stain a cell surface antigen, generally called as a CD marker, with a fluorescent labeling antibody specific thereto, and is used, for example for cell separation using a cell sorter, and a cancer screening using a flow cytometer or tissue staining. Naturally, these are frequently used not only in the medical field but also for the cytophysiological study and the industrial use of cells.
3) Alternatively, for separation of stem cells, fluorescent pigments designed to be taken into cells are used as reporters to roughly separate cells including stem cells and further then actually culture the cells, thereby separating target stem cells. Since an effective marker for a stem cell has not yet been established, the target cells are substantially separated by making use of only cells whose differentialtion has been induced by their actual culture.

Separating and collecting specific cells in a culture medium in this manner is an important technique for biological and medical analyses. When cells are separated based on a difference in the specific gravity of the cells, the target cells can be separated by a velocity sedimentation method. However, when there is little difference in the specific gravity of the cells that allows distinguishing between a non-sensitized cell and a sensitized cell, it is necessary to separate the cells one by one based on information from staining with a fluorescent antibody or information from visual observation.

This technique may be represented by, for instance, a cell sorter. The cell sorter is a technique in which a cell after fluorescent staining processing is dropped in a charged droplet as isolated one by one, and a high electric field is applied in any direction on the plane normal to the dropping direction in the process of the droplet dropping, where the dropping direction of the droplet is controlled by the applied voltage, based on the presence or absence of the fluorescence in the cell in the droplet and the amount of light scattering, to fractionate and collect the droplet in a plurality of containers placed at the bottom (Non Patent Literature 1: Kamarck, M. E., Methods Enzymol. Vol. 151, p 150-165 (1987)).

However, this technique involves the following problems: the cost is high; the system is large; a high electric field of some thousand volts is required; a large amount of samples concentrated to a certain concentration or more is required; cells may be damaged in the process of generating droplets; the samples cannot be directly observed. To solve these problems, a cell sorter has been recently developed which generates a fine flow path using microfabrication technology and separates cells flowing through the laminar flow in the flow path while directly observing the cells under a microscope (Non Patent Literature 2: Micro Total Analysis, 98, pp. 77-80 (Kluwer Academic Publishers, 1998)), Non Patent Literature 3: Analytical Chemistry, 70, pp. 1909-1915 (1998)). However, the following problems occur. Since the cell sorter which generates a fine flow path using the microfabrication technology is slow in the response speed of the sample separation with respect to an observation unit, another processing method that does not damage the samples and is faster in response is required in order to put the cell sorter into practical use. Further, the separation efficiency of the device cannot be improved sufficiently at a low cell concentration unless the concentration of the cells in a sample solution used is increased in advance to a predetermined concentration or more. Furthermore, when the cells are concentrated in a very small amount of a sample using a separated device, it is difficult to collect the concentrated solution without loss and at the same time the cells are contaminated at a cumbersome preprocessing stage, which is undesirable in regeneration medicine and the like.

In order to solve the problems, the present inventors have developed a device for cell analysis and separation capable of fractionating samples based on fine structures of the samples and fluorescence distribution in the samples and easily analyzing and separating the cell samples without damaging the samples collected, by utilizing microfabrication technology (Patent Literature 1: Japanese Patent Laid-Open No. 2003-107099, Patent Literature 2: Japanese Patent Laid-Open No. 2004-85323, Patent Literature 3: International Publication No. WO 2004/101731). This device is a sufficiently practical cell sorter at a laboratory level. However, for its versatile use in regeneration medicine, it is necessary to develop new techniques for a liquid transport method, a colletion method, and preprocessing such as sample preparation.

LIST OF PRIOR ART DOCUMENTS

Patent Literature

Patent Literature 1: Japanese Patent Laid-Open No. 2003-107099

Patent Literature 2: Japanese Patent Laid-Open No. 2004-85323
Patent Literature 3: International Publication No. WO 2004/101731

Non Patent Literature

Non Patent Literature 1: Kamarck, M. E., Methods Enzymol. Vol. 151, p 150-165 (1987)
Non Patent Literature 2: Micro Total Analysis, 98, pp. 77-80 (Kluwer Academic Publishers, 1998)
Non Patent Literature 3: Analytical Chemistry, 70, pp. 1909-1915 (1998)

SUMMARY OF THE INVENTION

Problem to be Solved by the Invention

When a micro flow path is formed on one surface of a substrate and a liquid is allowed to flow therethrough, the liquid flowing therethrough generally becomes a laminar flow. At a glance, it appears as if there were no flow rate distribution in the direction perpendicular to the flow direction. However, when a cell suspension is actually allowed to flow through such a micro flow path, a phenomenon frequently occurs in which cells contact a wall in the flow path. Since the cells in contact with the wall receive a resistance against the flow, the flow rate is decreased and thus the cells may contact other cells flowing from behind. When such a phenomenon occurs in a cell sorter or a flow cytometer, it becomes difficult to sort and detect the cells. In order to avoid such a phenomenon, a sheath flow technique is used in general. This sheath flow technique is to array the cells in line by allowing the cell suspension to flow into a core of the liquid flow flowing at a high rate as a sheath, which is achieved by uniting the sheath flow and the core flow and discharging the same into air as a jet flow. Since there is no wall in the conventional method, the cells can be sorted in an ideal state where the cells do not contact the wall.

However, it is extremely difficult to stably form the jet flow using the sheath. A practical system is very expensive, and cells for forming the sheath are not replaceable for each sample. Not only concerning a large-sized system but also concerning a cell sorter formed on a chip, all of the conventional techniques other than the method disclosed by the inventors of the present invention use independent pumps for delivering a sample liquid and for delivering a sheath liquid. These pumps are placed separately from the chip, and need to be reconnected every time the chip is replaced. It is also necessary to readjust the balancing fluctuation between the sample liquid delivery speed and the sheath liquid delivery speed accompanied with the replacement of the chip. To perform such precise control, large-sized and highly stable pumps are required. When the cells are arranged by introducing a sheath liquid, it is necessary to introduce a large amount of side sheath liquid. Thus, the concentration of the cells is unfavorably diluted.

Further, in the conventional cell sorter, in order to sort a target cell to be retrieved, a label such as a fluorescent antibody which can be optically identified is bound to the target cell and the label is identified by an optical method using a fluorescent detector or the like to be judged by an electronic method. Then, cells are sorted and purified. The cells are damaged by a labeling means and thus it becomes difficult to recultivate and replant the cells.

Solution to Problem

It is an object of the present invention to establish a cell concentrating and separating technique for reliably detecting and separating predetermined cells for the purpose of cell separation or detection using a flow path formed on one surface of a substrate, and to provide a device for concentrating and separating cells which can separate the cells continuously after a preparation process without contaminating the cells by including means for executing the cell concentration preparation process in which a cell concentration is not required to be adjusted in advance.

Also, it is an object of the present invention to provide a system for optically recognizing a shape of each of cells arranged in line as an image to retrieve the cells without labeling, and for identifying and retrieving the cells by an electronic means based on the image data of the shape of each cell.

Further, it is an object of the present invention to provide a system for retrieving only cells attracted to or repelled from electrophoresis force of a plurality of different frequencies in predetermined combination by the difference in responsiveness between cells arranged in line attracted to or repelled from an electrophoresis force of a predetermined frequency and by the fact that both of the cells having the repulsive force and the cells having the attracting force are concentrated to an acute end of a V-shape of an interdigitated electrode.

A cell assumed in the present invention ranges from a bacteria at the smallest to an animal cell such as a cancer cell at the largest. Therefore, the diameter of the cell ranges approximately from 0.5 µm to 30 µm. To concentrate and separate cells using a flow path incorporated in one surface of a substrate, the first problem is the width of the flow path (cross-sectional dimension). The flow path is formed on one surface of the substrate in a space of approximately 10 to 100 µm in the thickness direction of the substrate substantially in a two-dimensional plane. Based on the size of the cell, the suitable size of the flow path is 5 to 10 µm for the bacteria, and 10 to 50 µm for the animal cell.

The device for concentrating and separating cells according to the present invention includes a cell concentration portion having means for concentrating the cells, a cell arrangement portion and cell separation portion having means for separating and purifying the cells, and an optical analyzer for identifying and judging the separated and purified cells in the same chip. The cell concentration portion has a basic structure for introducing a sample liquid, which is not concentrated, from one inlet and discharging the sample liquid through an outlet disposed downstream of the concentration portion. In addition, the cell concentration portion includes means for concentrating the cells by imparting an external force to the cells toward a concentrated cell retrieving port disposed in a side wall of the concentration portion. As the external force, an ultrasonic radiation pressure, a gravitational force, an electrostatic force, or a dielectrophoretic force may be used. The external force is applied in the direction orthogonal to the flow of the sample liquid in the concentration portion and in the direction toward the concentrated cell retrieving port.

In the portion for separating and purifying the cells includes means for applying the external force to the cells to arrange the cells at the center of the flow path through which the cells flow and flowing all cells into one of two branched flow paths disposed on the downstream, and means for further applying the external force to only cells to be retrieved among the arranged cells to move the flow of the cells to be retrieved and introducing the cells to be retrieved into the other flow path of the two branched flow paths only when the external force is further applied. Specifically, by applying the external force, means for arranging cells in a node of standing wave by an ultrasonic radiation force, means for arranging cells at the vertex of a wedge-shaped electrode array, or means for arranging cells between a pair of electrodes using a pair of electrodes with whiskers. By using such means, cells can be arranged in line without adding a side sheath liquid. Thus, the problem to be solved by the present invention, in which a cell liquid concentrated in advance is diluted, can be solved.

In the portion for separating and purifying the cells includes means for applying the external force to the cells to arrange the cells at the center of the flow path through which the cells flow and flowing all cells into one of two branched flow paths disposed on the downstream, and means for further applying the external force to only cells to be retrieved of the arranged cells to move the flow of the cells to be retrieved and introducing the cells to be retrieved into the other flow path of the two branched flow paths only when the external force is further applied. Specifically, by applying the external force, means for arranging cells in a node of standing wave by an ultrasonic radiation pressure, means for arranging cells at the vertex of a wedge-shaped electrode array, or means for arranging cells between a pair of electrodes using a pair of electrodes with whiskers. By using such means, cells can be arranged in line without adding a side sheath liquid. Thus, the problem to be solved by the present invention, in which a cell liquid concentrated in advance is diluted, can be solved.

A cell detection portion in the device for concentrating and separating cells according to the present invention is provided in the cell separation portion. When a cell is captured as an image to be evaluated, an area to be observed by a CCD camera is provided upstream of a flow path branched portion. A cell separation area is provided downstream thereof as needed. When the cell passing through the flow path is irradiated by laser, and a scattering light or fluorescence are bound to the cell flowing, the fluorescence may be detected by a light detector without using the image of the cell. At this time, a separation flow path point serving as the cell separation area is provided downstream of the detector.

The cells are separated in the separation portion in the cell separation area. For example, when a dielectrophoretic force is applied to the cells as an external force from the outside for moving the cells in the cell separation portion, a pair of interdigitated electrodes and a flow path for separating and discharging the cells are provided. When an electrostatic force is applied as the external force, the positions of the cells in the flow path are changed by applying voltage to the electrodes. At this time, the cells are negatively charged and thus moved toward the positive electrode.

Also, since the pressure for introducing the sample liquid into the chip is used as the drive force for moving the liquid according to the present invention, it is preferable that pressures in a waste liquid outlet of the concentration portion, a purified cell outlet of the cell separation portion, and a waste liquid outlet of the cell separation portion are approximately equalized. Thus, a flow path resistance adjustment portion such as a thin flow path and an S-shaped long flow path for adjusting the pressure is arranged immediately before each outlet.

The algorithm of the recognition and sorting of the cells have the following features.

For capturing a cell as an image for evaluation, an area is provided in which the post-merging flow path can be observed with a CCD camera. The measuring range is expanded two-dimensionally to identify and trace the cell by image recognition. Thus, cell separation is performed with certainty. The important element at this point is the image capturing rate. With a general camera with a video rate of 30 frames/sec., all the cells cannot be imaged. A video rate of at least 200 frames/sec. is required to recognize the cells flowing in the flow path at high rate.

Next, the image processing method will be described. When the image-capturing rate is high, complicated image processing cannot be performed. Regarding the cell recognition, the cell moving velocity varies depending on each cell, and one cell may go past another cell as described above. Therefore, when each cell appears in an image frame for the first time, the cell is numbered. The same cell is managed with the same number until the cell disappears from the image frame. In other words, how an image of each cell is moved in a plurality of continuous frames is managed with the number. The cell in one frame and the same cell in another frame are linked with the condition that a cell is moved from the upstream to the downstream in each frame and that the moving velocity of a specified numbered cell recognized in the image is within a certain range. Thus, even if one cell goes past another cell, each cell can be traced with certainty.

In this manner, it becomes possible to recognize the cells. For numbering a cell, a cell image is binarized and the center of gravity thereof is obtained. The luminance center of gravity, area size, circumferential length, longer diameter and shorter diameter of the binarized cell are obtained, and each cell is numbered using these parameters. At this point, each cell image is automatically stored as an image because it is beneficial to the user.

In cell separation, only specific cells among the numbered cells need to be separated. The index for separation may be the information on the above-mentioned luminance center of gravity, area size, circumferential length, longer diameter, shorter diameter, or information obtained by fluorescence detection performed in addition to the image capturing. In any way, the cells detected in the cell detection area are separated in accordance with the numbers. More specifically, the moving velocity (V) of each numbered cell is calculated from images taken at an interval of a predetermined time period. A voltage is applied to a cell of a target number when such a cell is between the electrodes at a timing of (L/V) to (L/V+T), where L denotes the distance from the cell detection area to the cell separation area and T denotes the application period. In this manner, the cells are electrically separated.

Specifically, a device for concentration and separation cells as described below is provided according to the present invention.

(1) A cell separation chip including: a substrate; a flow path formed on the substrate and configured to allow a sample liquid containing cells to flow down; a cell concentration area provided in the flow path and configured to concentrate the cells; and a cell separation area provided in the flow path and configured to separate the cells.

(2) The cell separation chip as described in (1), in which the flow path is branched downstream of the cell concentration area, the sample liquid containing the cells passing through the cell concentration area is delivered into one of the branched flow paths, and the cell separation area is provided in the one of the branched flow paths.

(3) The cell separation chip as described in (2) including a cell information detection area upstream of the cell separation area in the branched flow path, in which the cells are separated in the cell separation area based on information relating to the cells detected in the cell information detection area.

(4) The cell separation chip as described in (2) or (3), in which the branched flow path is further branched downstream of the cell separation area, and the sample liquid containing the cells separated in the cell separation area is delivered into one of the further branched flow paths.

(5) The cell separation chip as described in any of (1) to (4) including a mechanism for applying an ultrasonic radiation pressure, a gravitational force, an electrostatic force, or a dielectrophoretic force to the cells in the cell concentration area.

(6) The cell separation chip as described in (5), in which the mechanism includes an electrode disposed on a surface of the flow path in the cell concentration area.

(7) The cell separation chip as described in (6), in which the electrode is an interdigitated electrode array.

(8) The cell separation chip as described in (7), in which the interdigitated electrode array comprises an array of V-shaped electrodes, and a vertex of a V-shape of each V-shaped electrode is oriented toward a downstream of the flow path.

(9) The cell separation chip as described in (1), in which the cell concentration area and the cell separation area are integrated in the flow path.

(10) The cell separation chip as described in (9), in which the interdigitated electrode array comprising the array of V-shaped electrodes is arranged on one surface of the flow path in the integrated cell concentration area and cell separation area so that the vertex of the V-shape of each V-shaped electrode is oriented toward the downstream of the flow path.

(11) The cell separation chip as described in (10), in which the flow path is branched downstream of the integrated cell concentration area and cell separation area, and the cells separated in a direction away from the electrodes or in a direction approaching the electrodes in the flow path are delivered into each branched flow path.

(12) A device for concentrating and separating cells including: (a) a cell separation chip including (i) a substrate, (ii) a flow path formed on the substrate and configured to allow a sample liquid containing cells to flow down, (iii) a cell concentration area provided in the flow path and configured to concentrate the cells, (iv) a cell information detection area provided downstream of the cell concentration area in the flow path and configured to obtain information relating to the cells, and (v) a cell separation area provided downstream of the cell information detection area in the flow path and configured to separate the cells; (b) a mechanism configured to apply an ultrasonic radiation pressure, a gravitational force, an electrostatic force, or a dielectrophoretic force to the cells in the cell concentration area; (c) a cell information detector including an optical system and a cell image processing unit configured to obtain information relating to the cells passing through the cell information detection area; and (d) a mechanism configured to apply a voltage to apply an external force to the cells in the cell separation area based on the information relating to the cells obtained by the cell information detector.

(13) The device for concentrating and separating cells as described in (12), in which the mechanism described in (b) includes an electrode arranged on a surface of the flow path in the cell concentration area.

(14) The device for concentrating and separating cells as described in (13), in which the electrode is an interdigitated electrode array.

(15) The device for concentrating and separating cells as described in (14), in which the interdigitated electrode array comprises an array of V-shaped electrodes, and a vertex of a V-shape of each V-shaped electrode is oriented toward a downstream of the flow path.

(16) The device for concentrating and separating cells as described in (12) including: a substrate; a first flow path provided on one surface of the substrate and configured to allow a liquid containing cells to flow down; an introduction inlet configured to introduce the liquid into the first flow path; a mechanism configured to concentrate the cells flowing down in the first flow path; a waste liquid outlet arranged at one end of the first flow path and configured to discharge a waste liquid remaining after the cells are concentrated; a second flow path connected to the first flow path and configured to branch the liquid containing the concentrated cells; a mechanism configured to arrange the cells in a straight line in the second flow path while flowing the concentrated cells; a cell information detector configured to detect a state of each cell in a predetermined area in the second flow path after arranging the cells; a cell separator provided downstream of the cell information detector in the second flow path and configured to allow the cells to flow down into one of two branched flow paths further downstream of the second flow path in accordance with information relating to the detected cell; and two liquid tanks provided downstream of the two branched flow paths and configured to hold a buffer liquid containing the cells flowing through the branched flow paths.

(17) The device for concentrating and separating cells as described in (16), in which the substrate is a plastic substrate formed by injection molding with a die, and the flow path is formed of a groove formed on one surface of the plastic substrate and a laminate film covering the groove.

(18) The device for concentrating and separating cells as described in (16), in which the information relating to the cell detected in the cell information detection area is obtained from information relating to an image of the cell.

(19) The device for concentrating and separating cells as described in (16), in which an ultrasonic radiation pressure, a dielectrophoretic force, or a dielectrophoretic force generated using an electrode array having a repeated structure of interdigitated electrodes having an acute end oriented toward a central portion downstream of the second flow path where the cells are desired to be concentrated, is are used as the mechanism configured to arrange the cells.

(20) The device for concentrating and separating cells as described in (16), in which a pair of interdigitated electrodes are provided in the second flow path through which the cells are delivered with a buffer liquid as the cell separating means, and the cells are divided into either one of two branched flow paths in the cell separation area depending on whether an alternating current is delivered between the two electrodes or not.

(21) The device for concentrating and separating cells as described in (16), in which one introduction inlet for introducing the liquid is provided in the first flow path and three or more waste liquid outlets are provided in the first flow path and the second flow path, and a flow path serving as an adjustment portion for adjusting a pressure is added immediately before the three or more waste liquid outlets to equalize a pressure as a drive force for moving the liquid introduced from the introduction inlet at the three or more outlets.

(22) A device for concentrating and separating cells including: (a) a cell separation chip including (i) a substrate, (ii) a flow path formed on the substrate and configured to allow a sample liquid containing cells to flow down, (iii) a cell concentration area and a cell separation area integrated in the flow path, and (iv) an interdigitated electrode array comprising an array of V-shaped electrodes arranged on one surface in the flow path in the integrated cell concentration area and cell separation area so that a vertex of a V-shape of each V-shaped electrode is oriented toward a downstream of the flow path; and (b) a mechanism configured to apply an AC electric field of a predetermined frequency to apply a dielectrophoretic force of a predetermined frequency depending on the cells to be separated to the interdigitated electrode array.

(23) The device for concentrating and purifying cells as described in (22), in which the predetermined frequency of the AC electric field is varied.

(24) The device for concentrating and separating cells as described in (22) or (23), in which the flow path for the cell separation chip is branched downstream of the integrated cell concentration area and cell separation area, and the cells separated in a direction away from the electrodes or in a direction approaching the electrodes in the flow path are delivered into each branched flow path.

(25) A device for concentrating and separating cells including a plurality of the devices for concentrating and separating cells as described in (24), in which at least one of the branched flow paths is connected to an upstream end of a flow path configured to allow the sample liquid containing the cells in another device for concentrating and separating cells to flow down, and the plurality of devices for concentrating and separating cells are arranged in tandem so that the liquid containing the cells flowing through the at least one of the branched flow paths is further concentrated and separated in the other device for concentrating and separating cells.

Advantageous Effects of the Invention

By using the device for concentrating and separating cells according to the present invention, a cell concentrating and separating technique for reliably detecting and separating a predetermined cell for the purpose of cell separation or detection using a flow path formed on one surface of a substrate can be established. Further, since the device for concentrating and separating the cells includes means for executing a cell concentration preparation process in which a cell concentration is not required to be adjusted in advance, the cells are separated continuously after the preparation process without contaminating the cells.

In a conventional cell sorter formed on a chip, cells introduced into the cell sorter are concentrated through a concentration process using a centrifugal separator or the like that is separately provided, and accordingly, the cells are contaminated. However, according to the present invention, cells are concentrated directly on a chip, and a portion for delivering a liquid and a tank for cultivating the cells are also formed on the chip. Because functions other than optical system are employed only on the chip, the cells are not contaminated with no loss. Further, the procedure can be simplified and the processing time is shortened to improve usability. For example, for stem cell separation or clinical examination, the prevention of contamination of cells derived from a specimen tissue is required. However, the contamination needs not to be considered. Since main processes including the preparation process of the cell sorter are conducted on the chip as described above, the cross contamination of the device can be completely prevented. A cell separation system in which the cross contamination is prevented and which is required in the field of medicine, especially in the field of regeneration medicine, is provided.

According to the present invention, a single-use device for concentrating and separating cells without contamination which does not require pre-treatment such as cell concentration and which can separate the cells stably can be provided.

DESCRIPTION OF EMBODIMENTS

Embodiments of the present invention will be explained below in detail with reference to the accompanying drawings, but the present invention is not limited thereto.

(System Structure of Device for Concentrating and Separating Cells)

Figure 1:
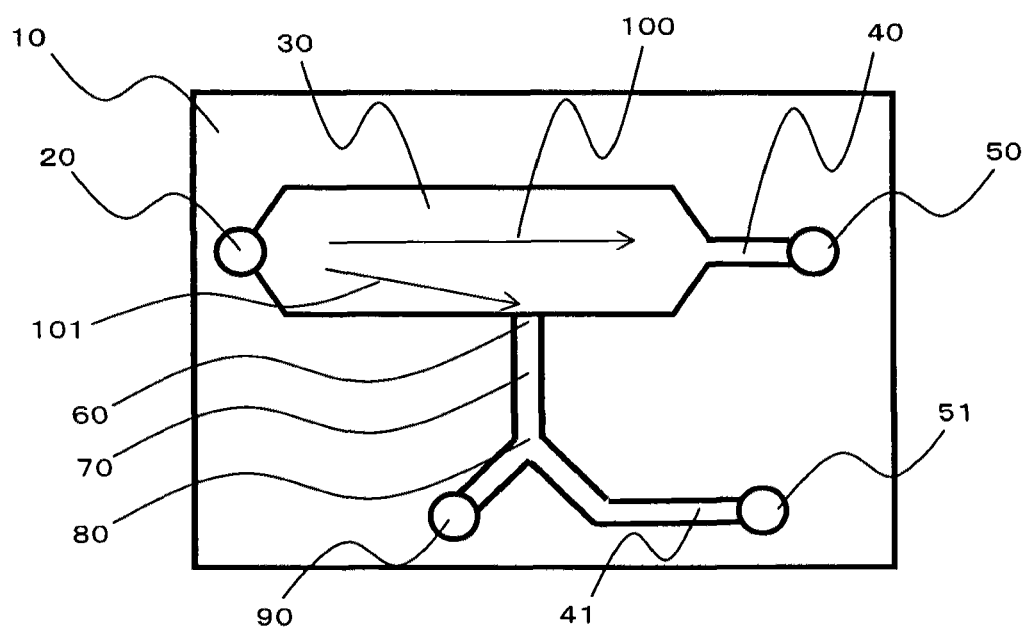
FIG. 1 is a schematic view schematically showing one example of a system structure of a device for concentrating, separating and cultivating cells according to the present invention.

FIG. 1 is a plan view schematically showing a basic outline of a system structure of a device for concentrating and separating cells according to the present invention. For concentrating, arranging, and purifying cells in a sample liquid, the device includes a series of fine flow paths arranged two-dimensionally on a planar chip 10 and means for applying a force to the cells in the chip 10.

The device 1 for concentrating and separating cells is provided on the chip 10. The flow paths are provided in the chip 10 and an opening communicating to the flow paths are provided on an upper surface serving as a supply opening for samples and necessary buffer solutions (mediums). The flow paths may be formed by so-called injection molding, by which a plastic material such as PMMA is injected into a mold. Alternatively, the flow paths may be formed by connecting a plurality of glass substrates. The chip 10 has an overall size of 50×70×1 mm(t), but it is not limited thereto. To observe cells flowing through the flow paths or wells formed from grooves or through-holes on the inner surface of the chip 10 by a high-powered optical microscope, a 0.1 mm thick laminate film provided by thermal pressurization may be used when a PMMA plastic material is used. When a glass material is used, a 0.1 mm thickness glass provided by optical adhesion may be used. For example, using an objective lens having a numerical aperture of 1.4 and a magnification of 100, the cells flowing through the flow paths can be observed through the 0.1 mm thick laminate film. In the case where the plastic material is highly light-transmissive, such cells can be observed also from above the chip substrate 10. A cell assumed in the present invention ranges from a bacteria at the smallest to an animal cell such as a cancer cell at the largest. Accordingly, the cell size is typically in the range of approximately 0.5 μm to 30 μm, but it is not strictly limited thereto. As long as the present invention is effectively used, cells of any size may be used. To concentrate and separate cells continuously using the flow paths incorporated in one surface of the substrate, the first problem is the width of the flow path (cross-sectional dimension). The flow path is typically formed on one surface of the substrate in a space of approximately 10 to 100 μm in the thickness direction of the substrate substantially in a two-dimensional plane. Based on the size of the cell, the suitable size of the flow path is 5 to 10 μm for the bacteria, and 10 to 50 μm for the animal cell.

First, a sample liquid is introduced from a sample liquid inlet 20 into a cell concentration portion 30 on the chip 10 by a syringe pump or cell introducing means such as air pressure which does not generate a pulsatile flow. The sample liquid containing cells introduced into the cell concentration portion is delivered along a sample flow 100 toward a waste liquid outlet 50 downstream to be discharged. The cell concentration portion 30 includes means for continuously applying an external force to the cells to concentrate the cells toward a cell concentrate inlet 60 disposed on part of a side wall of the cell concentration portion 30. The cells are gradually concentrated along a concentrated cell flow 101 by the external force and a cell concentration liquid having high concentration 100 times or more higher than the concentration of the cells at the sample liquid inlet is introduced into the cell concentrate inlet 60.

As the external force to be applied to the cells, an ultrasonic radiation pressure, a gravitational force, an electrostatic force, or a dielectrophoretic force may be used. For example, when the ultrasonic radiation force is used, a traveling wave of an ultrasonic wave is generated in the direction orthogonal to the flow of the sample liquid and toward the cell concentrate inlet 60 so as to be generated the concentrated cell flow 101 by the radiation pressure of the ultrasonic wave. To introduce the ultrasonic wave, a PZT piezoelectric element may be attached to the surface of the chip 10. Alternatively, an interdigitated electrode array, which is disposed on a surface of a piezoelectric element to generate a surface acoustic wave in the cell concentration portion, may be attached to the surface of the cell concentration portion 30 to introduce the ultrasonic wave into the cell concentration portion. When the gravitational force is used, the arrangement of the chip may be adjusted so that the gravitational force is applied in the direction orthogonal to the flow of the sample liquid and toward the cell concentrate inlet 60. Alternatively, the chip may be disposed on a rotary disk so that the direction of the radius of the disk is the same direction as the direction orthogonal to the flow of the sample liquid and toward the cell concentrate inlet 60. When the electrostatic force is used, an electrode may be disposed on the side wall of the cell concentration portion 30 so that the cells receive the external force toward the side wall. At this time, a positive or negative charge may be applied depending on the potential of the surface of the cell to which the external force is applied. However, when the electrostatic force is applied, bubbles are generated on the electrode in the case where the charge of the surface of the electrode applying a current exceeds a peroxygenated charge or a certain charge such as a peroxygenated charge. Accordingly, the applied voltage is extremely small and thus the length of the flow path in the cell concentration portion 30 needs to be flexibly adjusted depending on the type of the external force applied to the cells and the strength thereof. The flow path needs to be sufficiently long when the electrostatic force is applied as the external force. When the dielectrophoretic force is used as the external force, the electrode may be disposed in the cell concentration portion 30 so that the dielectrophoretic force is applied in the direction orthogonal to the flow of the sample liquid and toward the cell concentrate inlet 60.

Next, cells in the concentrated cell liquid introduced into the cell concentrate inlet 60 are arranged in line along the flow of the liquid in a cell arrangement portion 70. More specifically, the cell arrangement portion 70 includes means for generating the external force to attract the cells to the central portion of the flow path in the cell arrangement portion 70 by using the dielectrophoretic force or the ultrasonic radiation pressure in a standing wave mode. The cells arranged in line at the center are measured and the type of each cell is determined in a cell detection area 221 arranged before a cell separation portion 80 (see FIG. 7). Then, the cells are delivered into a purified cell outlet 90 or a waste liquid outlet 51, which are provided in two divided downstream areas, depending on the presence or absence of the external force applied in the direction orthogonal to the flow from the upstream to the downstream.

Since only one sample liquid inlet 20 is provided in this embodiment, the force of the syringe pump or the like for introducing the sample liquid through the inlet can be used as the drive force for generating a series of flows of the liquid from the sample liquid inlet 20 toward three outlets, i.e., the purified cell outlet 90 and the waste liquid outlets 50 and 51. However, to equalize liquid flows from one inlet, the pressure needs to be equally dispersed toward the three outlets and three liquid flows need to be equally generated. To discharge the liquid equally, flow path resistance adjustment portions 40 and 41 are provided before the outlets, respectively. The pressure differences generated by positions of the outlets are offset by the flow path resistance adjustment portions 40 and 41. Practically, the flow resistance in the chip is provided by adding an S-shaped flow path and extending the length of the entire flow path, or narrowing the width of the flow path.

Further, by providing the flow path resistance adjustment portions as described above, the cells can be separated and purified in a plurality of steps. More specifically, a second cell concentrate inlet and a second cell separation portion may be provided after the cell concentrate inlet 60 and the cell separation portion 80 without providing an outlet at the position of the waste liquid outlet 51, so that the cells are separated and purified repeatedly. Accordingly, a plurality of types of cells can be picked and purified independently at one time.

Figure 2:
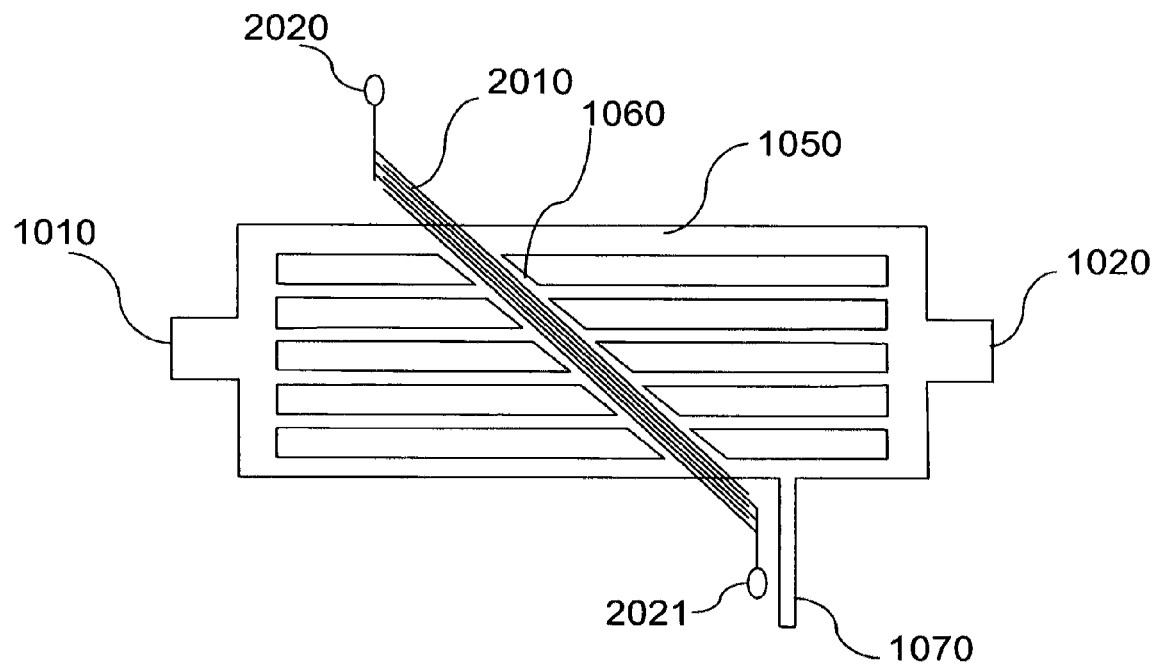
FIG. 2 is a plan view schematically showing one example of a structure of a cell concentration portion shown in FIG. 1.

FIG. 2 shows one example of the structure of the concentration portion 30 when the dielectrophoretic force is used as the external force. A sample liquid containing cells introduced from a sample liquid inlet 1010 is delivered into a waste liquid outlet 1020 through concentration portion parallel flow paths 1050. An oblique interdigitated electrode 2010 for concentration is provided in the middle of the concentration portion parallel flow paths 1050 to have a predetermined angle relative to the direction of liquid flows so that the dielectrophoretic force can be applied in the direction of a branched flow path for sorting concentrated particulates. For example, by applying an AC electric field of 30 Vpp at 1 MHz to a pair of connection points 2020 and 2021 at ends of the oblique interdigitated electrodes for concentration, the cells are continuously concentrated through a concentration portion oblique flow path 1060 and delivered toward the branched flow path 1070 for sorting concentrated particulates. When the flow rate is high, for example, approximately 20 m/s, the external force can be sufficiently applied to the cells to concentrate the cells in the case where the voltage is increased to approximately 350 Vpp.

Figure 3:
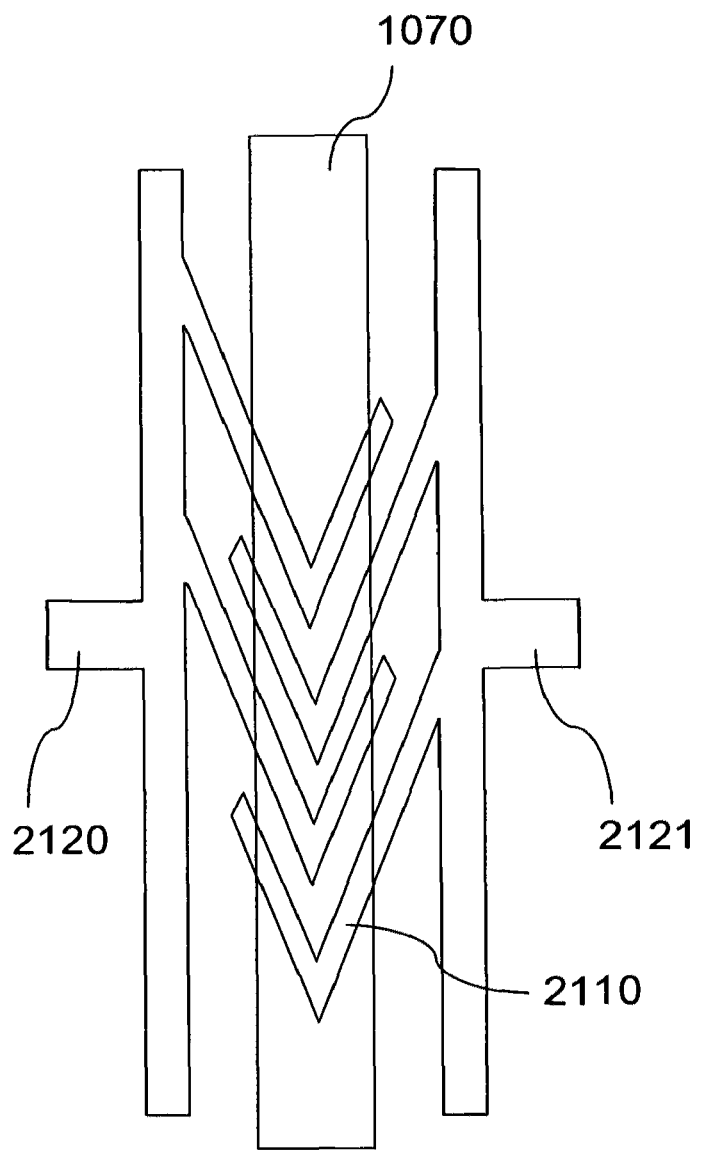
FIG. 3 is a plan view schematically showing one example of a structure of a cell arrangement portion shown in FIG. 1.
Figure 4:
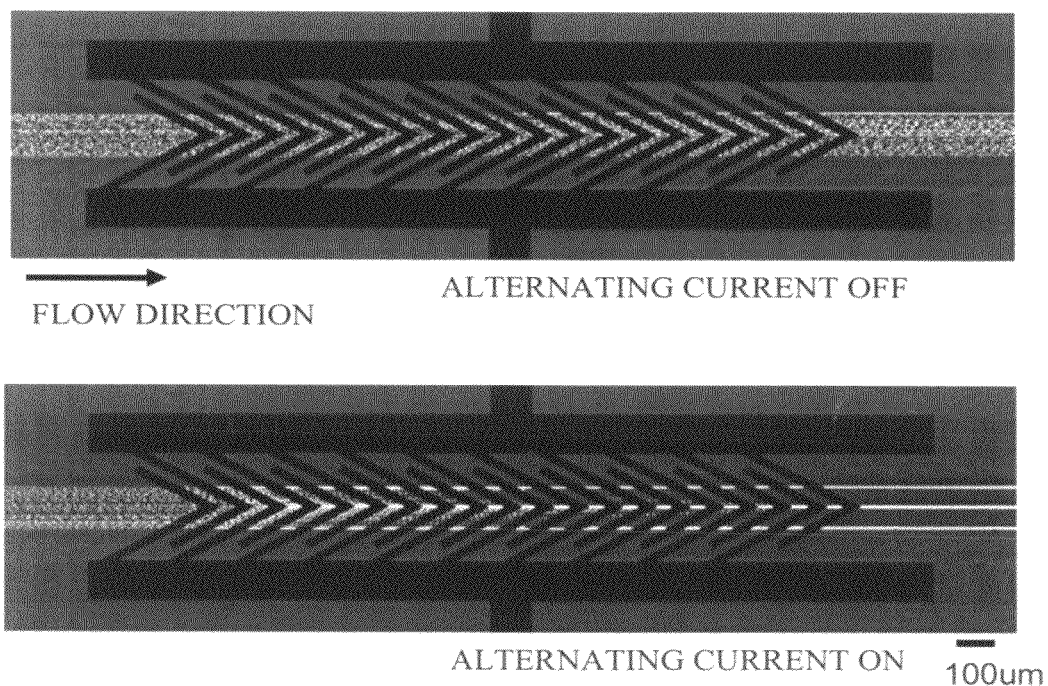
FIG. 4 shows results in which polystyrene particulates are actually arranged using wedge-shaped electrodes as one example of the structure of the cell arrangement portion shown in FIG. 1.

FIG. 3 shows one example of the structure of the cell arrangement portion when the dielectrophoretic force is used as the external force. The concentrated cell liquid introduced from the branched flow path 1070 for sorting concentrated particulates is delivered through the flow path in the cell arrangement portion. As shown in FIG. 3, electrodes (V-shaped interdigitated electrodes 2110 for convergence) are alternately arranged to have a wedge shape. By applying the voltage to connection points 2120 and 2121 of the V-shaped interdigitated electrodes 2110 for convergence, the external force can be applied to the cells toward the vertex of the wedge shape. Consequently, the cells are continuously concentrated at the vertex of the wedge shape. In this embodiment, the shape of the electrode arranged in the flow path is important. Since the electrode is an interdigitated electrode positioned obliquely toward the downstream side and is not flat to have an end of an acute angle and have an axis symmetry shape, the cells receiving the dielectrophoretic force are collected at the acute end of the electrode and arranged by the total force of the force by which the cells are delivered toward the downstream with the flow and the force which the cell receives toward the acute end whether the cells are attracted to or repelled from the dielectrophoretic force. In other words, by disposing the acute vertex of the electrode array at the position of the flow path where the cells are desired to be concentrated, the cells are collected at the acute end by the total force of the force by which the cells are delivered toward the downstream and the dielectrophoretic force in the direction toward the acute end. FIG. 4 shows one example of results when the cells are actually concentrated. An aluminum material is evaporated on a bottom surface of the substrate so that each wedge-shaped electrode having the width of 20 μm is provided by the interval of 20 μm to have the angle of 30 degrees relative to the liquid flow in the flow path having the width of 120 μm and the height (depth in the chip) of 12.5 μm. Polystyrene beads (the diameter of 2 μm) are dispersed in the solution of 0.5 mg/ml of BSA and 13.5% of sucrose and delivered at the flow rate of 1 mm/s. When the voltage is not applied, the particulates are delivered directly through the flow path. When the sine waves of 10 Vpp at 10 MHz are applied to the electrode, it can be observed that the polystyrene particulates are collected at the center of the flow path.

Figure 5:
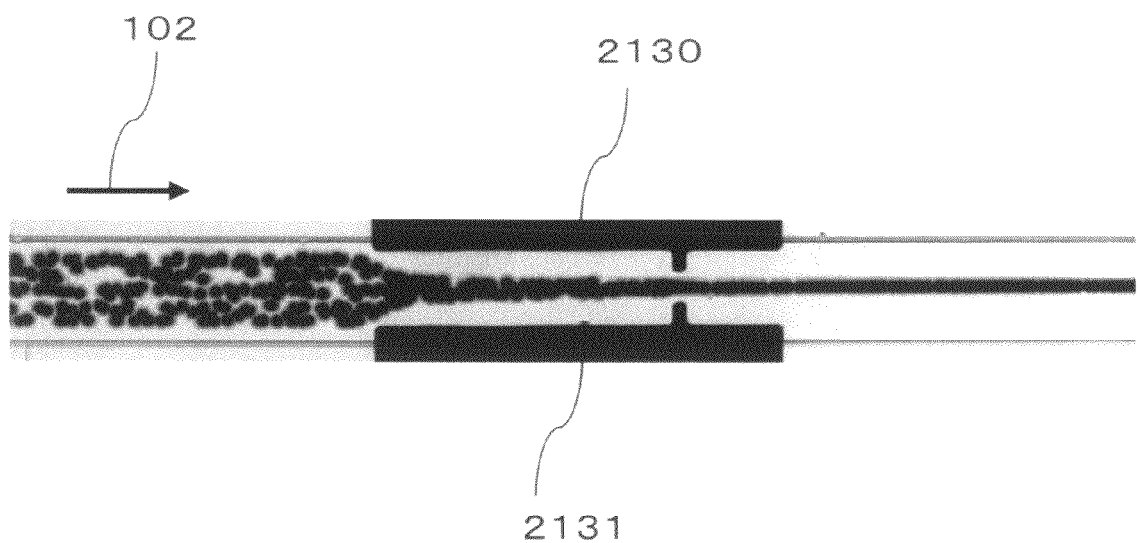
FIG. 5 shows a result in which polystyrene particulates are actually arranged using electrodes with whiskers as one example of the structure of the cell arrangement portion shown in FIG. 1.

FIG. 5 shows the same composition as that in FIG. 4 except that a pair of electrodes 2130 and 2131 with whiskers are provided as the electrodes. FIG. 5 shows another example of the results in which the polystyrene beads are arranged in line by applying the AC electric field to the electrodes with whiskers. As obvious from FIG. 5, the particulates delivered from the upstream can be arranged in line after passing through the cell arrangement portion in the flow path.

In the technique for arranging the cells as shown in FIGS. 3 to 5, the position where the cells are arranged in the flow in the cell arrangement portion is important. When the position is close to the waste liquid flow path from the center in the flow, the arranged cells are delivered directly into the waste liquid outlet 51 while the external force is not applied. Only cells moved close to the purified cell flow path by receiving the external force are collected in the purified cell outlet 90. When the position is close to the purified cell flow path from the center in the flow, the arranged cells are delivered into the waste liquid outlet 51 while the external force is continuously applied. When the position is returned to the original position by stopping the external force, only cells returning to be close to the purified cell flow path are collected in the purified cell outlet 90. In the former case, the external force is applied only when a cell which is desired to be picked up is delivered. However, the electric external force is applied to the cell. In the latter case, the electric external force is not applied to the cell to be picked up. However, the external electric field is required to be always applied to cells to be discarded.

Figure 6:
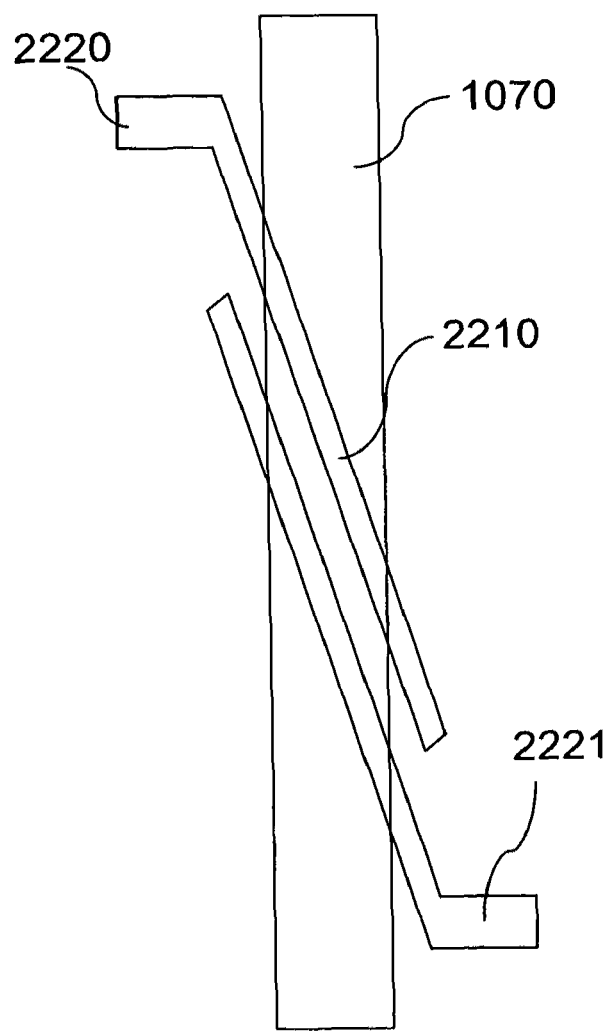
FIG. 6 is a plan view schematically showing one example of a structure of a cell separation portion shown in FIG. 1.

FIG. 6 shows one example of the cell separation portion when the dielectrophoretic force is applied to the cells as the external force. An electrode array having the same structure as the electrode used in the cell concentration portion shown in FIG. 2 is positioned to have a predetermined angle relative to the flow in the direction where the external force is desired to be applied. Accordingly, the cells arranged in line in the cell arrangement portion are arranged differently in another flow path on the downstream. By applying the AC electric field to connection points 2220 and 2221 at both ends of a pair of oblique electrodes 2210 for separation, the external force enough to separate the arranged cells delivered from the branched flow path 1070 for sorting concentrated particulates. In this embodiment, only a pair of electrodes, i.e., the minimum number of electrodes, are provided to minimize an area receiving the external force at one time so that the cells are operated in one-cell units by switching between the electrodes. This structure is different from that of the electrodes arranged for concentration as shown in FIG. 3.

(Example of Optical System)

Figure 7:
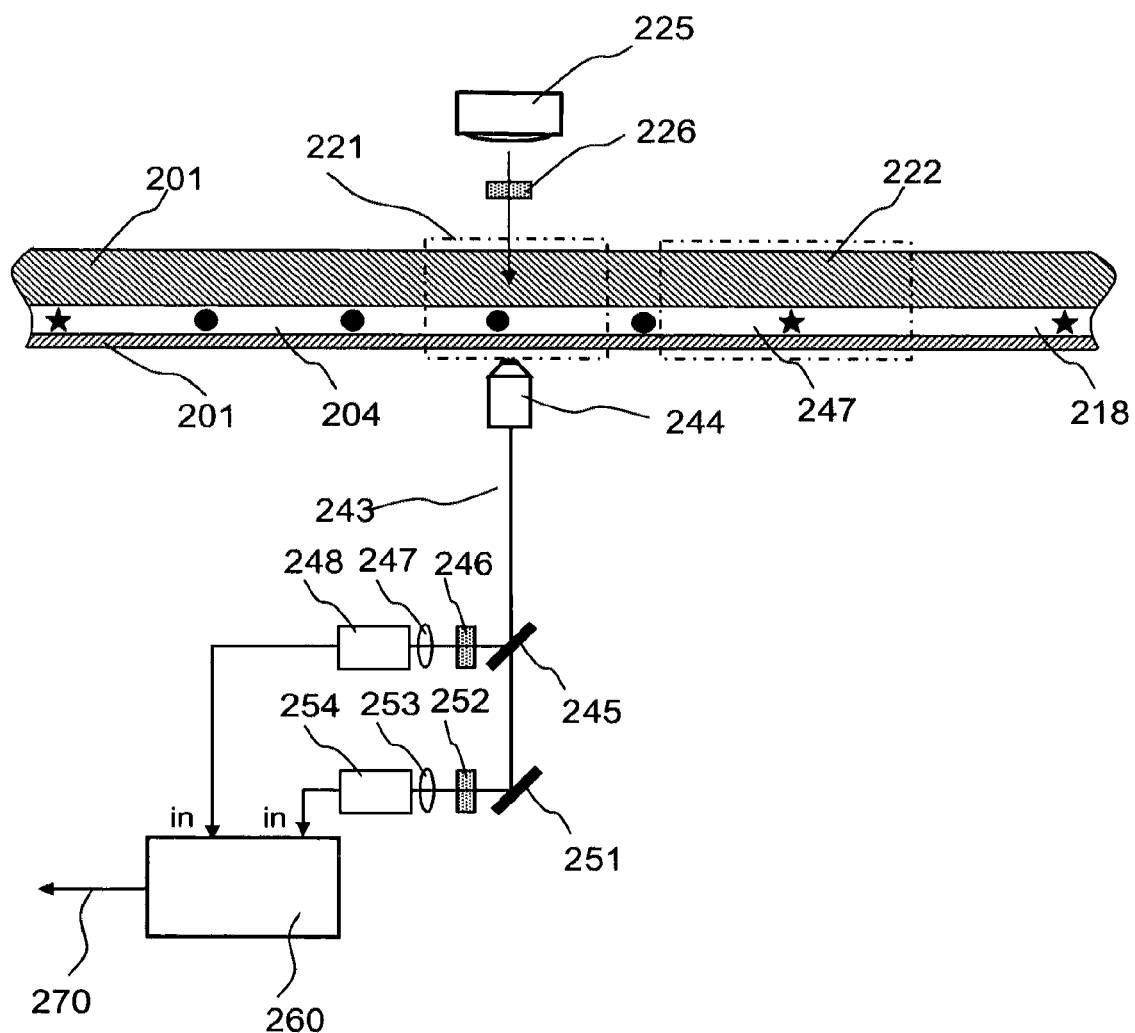
FIG. 7 is a conceptual diagram showing an outline of an optical system in a cell detection area.

FIG. 7 is a conceptual diagram showing an outline of an optical system in the cell detection area 221. A light source 225 for irradiating light to cells and a filter 226 are provided above a chip substrate 201 of a device for separating and cultivating cells. A detection system for the light irradiated to the cells is provided below the chip substrate 201. As obvious from FIG. 2, a cross-section of a flow path 218 from a cell detection area 221 to a cell separation area 222 is shown.

A cell flowing through the flow path 218 in the cell detection area 221 is irradiated by the light source 225 through the filter 226. An image of the cell irradiated with light is detected via an objective lens 244 and captured as fluorescence intensity data in a fluorescence detector 248 through a dichroic mirror 245, a filter 246, and a lens 247. The image of the cell is also captured as cell image data by a cell imaging camera 254 through a mirror 251, a filter 252, and a lens 253. The fluorescence intensity data obtained in the fluorescence detector 248 and the image data captured by the cell imaging camera 254 are transmitted to an information analyzer 260 including a computer which has an image processing function and determines the type of the cell so as to check the fluorescence intensity data and the image data against image data relating to a cell to be detected which is prepared in advance. When the captured data is determined to be the data of the cell to be picked up, the information analyzer 260 transmits a cell separation control signal 270. Then, a switch of the cell separation portion is turned on to apply the force to the cell in the cell separation portion 222. At this point, the moving velocity of cells flowing in the flow path (flow rate of buffer solution flowing in the flow path 204) is detected separately, so that the cell evaluated in the cell detection area 221 can receive the voltage when flowing through the cell separation area 247.

Here, the processing using an image and the processing using fluorescence or scattering light may be used in combination. Also, the image data captured by the camera 254 may be displayed on a computer monitor to be observed by a user. When there are a plurality of fluorescence to be observed, the filter 226 is adjusted appropriately to transmit a plurality of excitation light and irradiate to cells with light having a wavelength which is not the same as a wavelength of light for detecting subsequent fluorescence in the flow. A plurality of combinations of a dichroic mirror, a filter and a fluorescence detector can be used depending on the type of the florescence to be observed. With such a structure, the results from fluorescence observation in relation to images of the cells may be used as data.

The algorithm of the recognition and sorting of cells have the following features.

For capturing a cell as an image for evaluation, an area is provided in which the post-merging flow path can be observed with a CCD camera. The measuring range is expanded two-dimensionally to identify and trace the cell by image recognition. Thus, cell separation is performed with certainty. The important element at this point is the image capturing rate. With a general camera with a video rate of 30 frames/sec., all the cells cannot be imaged. A video rate of at least 200 frames/sec. is required to recognize the cells flowing in the flow path at high rate.

Next, the image processing method will be described. When the image-capturing rate is high, complicated image processing cannot be performed. Regarding the cell recognition, the cell moving velocity varies depending on each cell, and one cell may go past another cell as described above. Therefore, when each cell appears in an image frame for the first time, the cell is numbered. The same cell is managed with the same number until the cell disappears from the image frame. In other words, the movement of an image of each cell in a plurality of continuous frames is managed with the number. Under the conditions that cells present upstream side in one frame moves downstream in turn in successive frames and that the moving velocity of a numbered specific cell recognized in the image is within a certain range, a cell is linked between the frames. Thus, even if one cell goes past another cell, each cell can be traced with certainty.

In this manner, it becomes possible to recognize the cells. For numbering a cell, a cell image is binarized and the center of gravity thereof is obtained. The luminance center of gravity, area size, circumferential length, longer diameter and shorter diameter of the binarized cell are obtained, and each cell is numbered using these parameters. At this point, each cell image is automatically stored as an image because it is beneficial to the user.

In cell separation, only specific cells among the numbered cells need to be separated. The index for separation may be the information on the above-mentioned luminance center of gravity, area size, circumferential length, longer diameter, shorter diameter, or information obtained by fluorescence detection performed in addition to the image capturing. In any way, the cells detected in the cell detection area are separated in accordance with the numbers. More specifically, the moving velocity (V) of each numbered cell is calculated from the images taken at an interval of a predetermined time period. A voltage is applied to a cell of a target number over a time period of (L/V) to (L/V+T) during which the cell is between the electrodes, where L denotes the distance from the cell detection area to the cell separation area and T denotes time period for applying voltage. In this manner, the cells are electrically separated.

Figure 8:
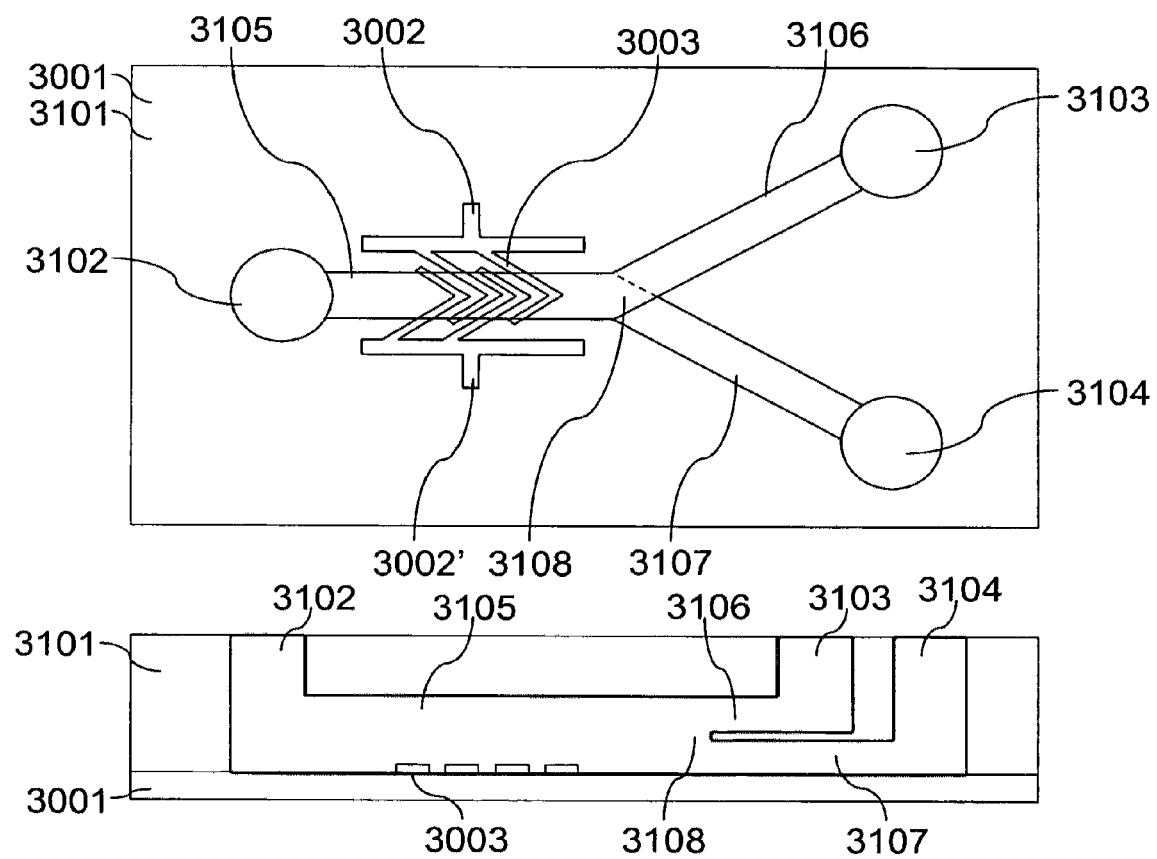
FIG. 8 includes a plan view (upper view) and a side view (lower view) schematically showing one example of a device for continuously separating and purifying particulates by difference in polarity of dielectrophoretic forces.

FIG. 8 shows one example of a technique for continuously purifying cells by difference between a repulsive force and an attracting force generated in cells against a dielectrophoretic force having a specified frequency. The important element at this point is that both of particulates having the repulsive force and particulates having the attracting force against the dielectrophoretic force of the specified frequency are collected at a vertex of an acute angle in an electrode having a V-shaped structure. However, the particulates having the repulsive force are not collected on a substrate on which the electrode is arranged and are collected on a substrate opposite to the substrate on which the electrode is arranged. The particulates having the attracting force are collected on the substrate on which the electrode is arranged. The structure of such a device will be explained below. FIG. 8 includes a plan view (upper view) and a side view (lower view) schematically showing one example of a device for continuously separating and purifying particulates by difference in polarities of the dielectrophoretic force. The device includes a thin-film electrode arranged on an electrode chip 3001 for generating the dielectrophoretic force, and a fine flow path arranged two-dimensionally which has three-dimensionally branched paths in a flow path chip 3101. An electrode chip 3001 and a flow path chip 3101 may be made of a transparent material such as a PMMA and a glass, so that particulates flowing in the flow path can be operated while being observed by an optical microscope. Alternatively, they may be made of an opaque material, so that particulates are operated without being observed. A sample liquid introduced from a sample liquid inlet 3102 is delivered through a dielectrophoretic force applying portion 3105 and is branched at a three-dimensional branched portion 3108 into an upper flow path 3106 and a lower flow path 3107 in the vertical direction of the flow path to be discharged through an upper flow path outlet 3103 and a lower flow path outlet 3104. An V-shaped interdigitated electrode 3003 is provided on a bottom surface of the dielectrophoretic force applying portion 3105 and is connected to an AC source via AC electrode connection points 3002 and 3002'.

Figure 9:
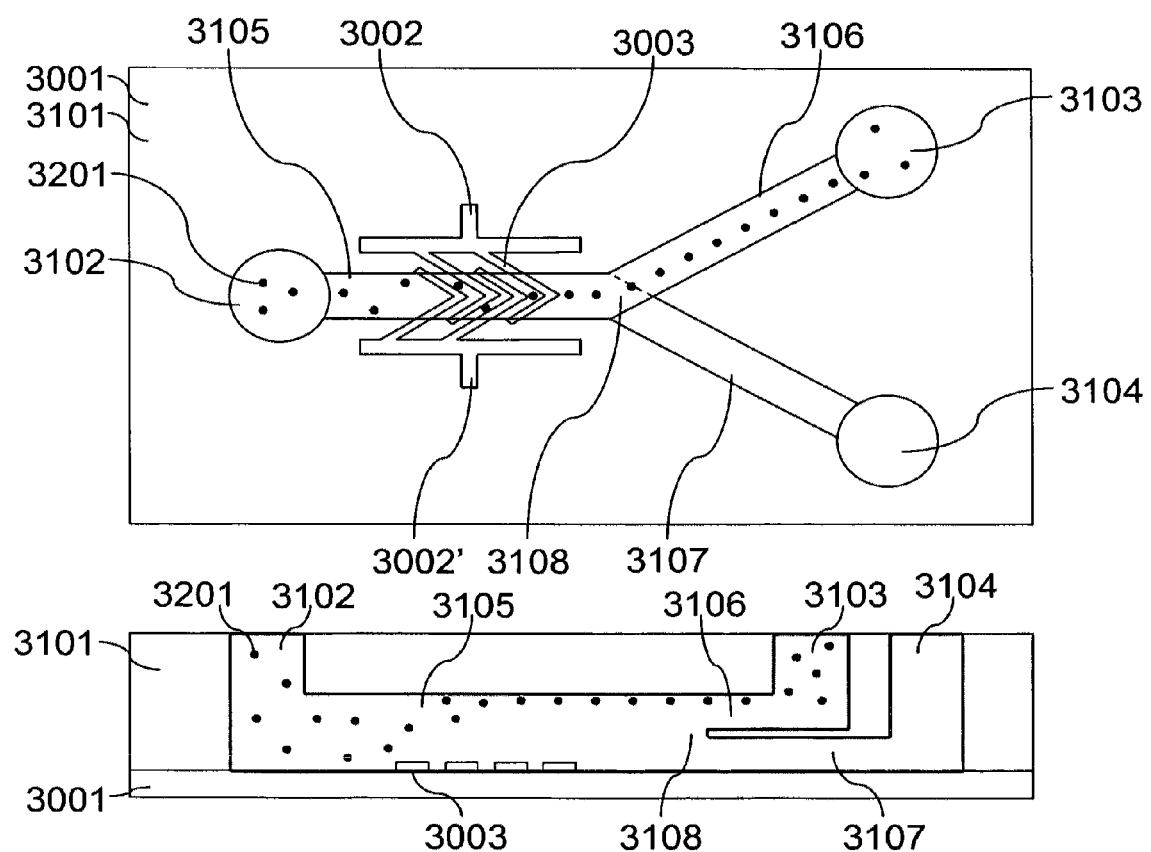
FIG. 9 includes a plan view (upper view) and a side view (lower view) of a conceptual diagram illustrating the principle of separating and purifying particulates when the particulates receiving a negative dielectrophoretic force are introduced into the device shown in FIG. 8.
Figure 10:
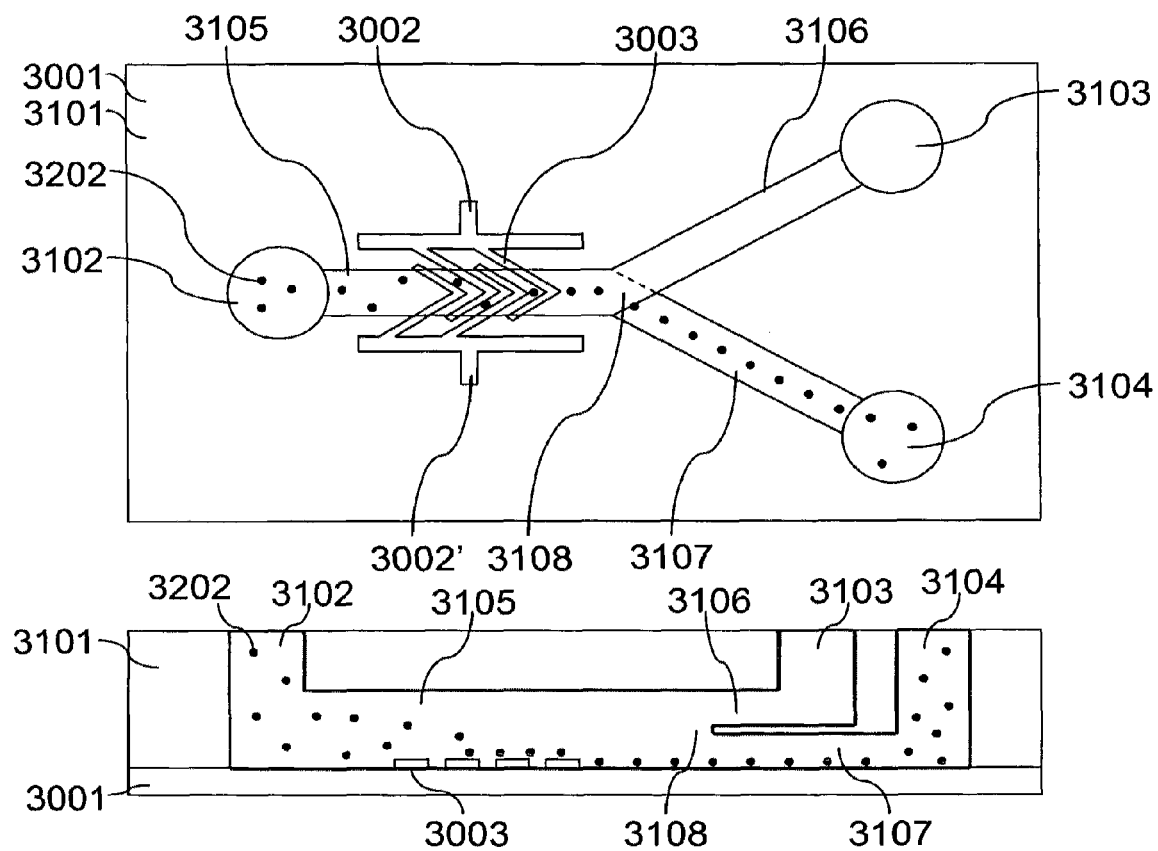
FIG. 10 includes a plan view (upper view) and a side view (lower view) of a conceptual diagram illustrating the principle of separating and purifying particulates when the particulates receiving a positive dielectrophoretic force are introduced into the device shown in FIG. 8.

FIGS. 9 and 10 show how particulates having the repulsive force against a specified frequency are actually moved. FIGS. 9 and 10 show one example of the movement. FIG. 9 (and FIG. 10) are conceptual diagrams illustrating the principle of separating and purifying particulates based on the difference in polarities of dielectrophoretic forces when the particulates receiving negative (positive) dielectrophoretic force are introduced into the device. Particulates 3201 (3202) introduced from the sample liquid inlet 3102 receive the repulsive force (attracting force) due to the dielectrophoretic force applied from the V-shaped interdigitated thin-film electrode 3003 when passing through the dielectrophoretic force applying portion 3105. Therefore, the particulates 3201 (3202) are concentrated at the center of the flow path in the planar direction and concentrated on an upper surface (lower surface) of the flow path in the vertical direction. Since the flow path is three-dimensionally branched at the three-dimensional branched portion 3108 in the vertical direction, the particulates are delivered only into the upper flow path 3106 (lower flow path 3107) and are not delivered into the lower flow path 3107 (upper flow path 3106). Thus, the particulates receiving the dielectrophoretic forces of different polarities can be exclusively separated and purified.

Figure 11:
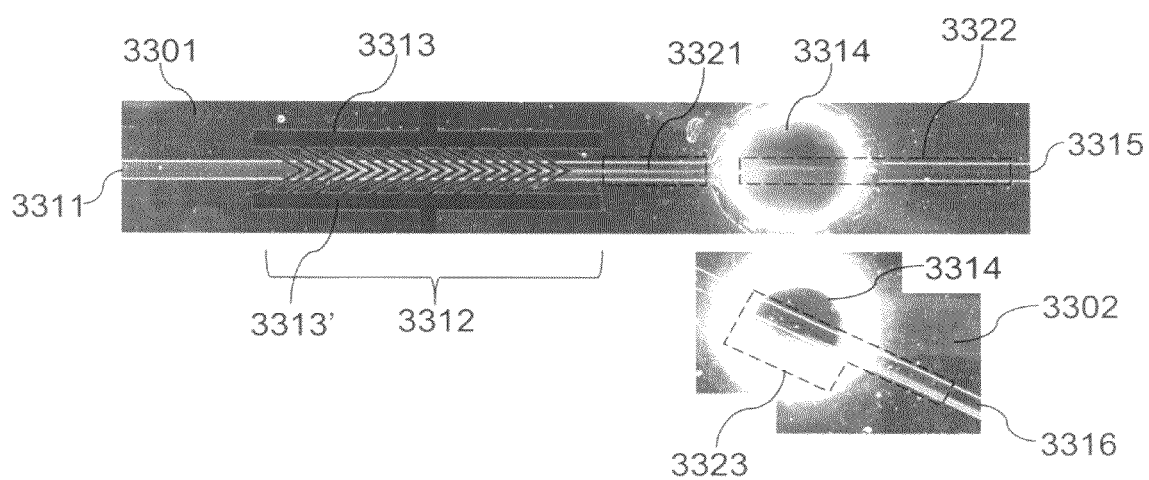
FIG. 11 shows a result in which Bacillus subtilis and polystyrene beads are actually separated and purified using V-shaped interdigitated electrodes as one example of a structure of the device for separating and purifying the particulates of which the structure is illustrated in FIG. 8 and of which the operation principals are illustrated in FIGS. 9 and 10.

FIG. 11 shows one example of a result of separation and purification of particulates by difference in polarities of the dielectrophoretic forces. The upper drawing 3301 shows a lower layer portion of a device, which includes a sample liquid inlet 3311, a dielectrophoretic force applying portion 3312, V-shaped interdigitated electrodes 3313 and 3313', and a lower flow path 3315. The lower drawing shows an upper layer portion of the device, which includes an upper flow path 3316. The flow path in a lower layer portion 3301 of the device is connected to the flow path in an upper layer portion 3302 of the device via a vertical flow path in a three-dimensional branched portion 3314. The dielectrophoretic force applying portion 3312, the lower flow path 3315, and the upper flow path 3316 are formed in a PDMS chip. Each of them has the width of 120 µm and the height (depth in the chip) of 10 µm. The vertical flow path in the three-dimensional branched portion 3314 has the diameter of 1 mm and the length of 1 mm. The V-shaped interdigitated electrodes 3313 and 3313' are arranged by the interval of 20 µm to have the width of 20 µm and the angle of 30 degrees relative to the flow path by evaporating an aluminum material to a glass substrate. Bacillusu subtilis and polystyrene beads having the diameter of 1 µm are dispersed in the solution of 0.5 mg/ml of BSA and 13.5% of sucrose and injected through the sample liquid outlet 3311 at the flow rate of 1.6 mm/s. When the AC voltage of 20 Vpp at 1 MHz is applied to the V-shaped interdigitated electrodes 3313 and 3313', both of the Bacillusu subtilis and polystyrene beads are collected at the center of the flow path in the planar direction (3321). It can be observed that the Bacillusu subtilis are delivered into the lower flow path 3315 (3322) by receiving the positive dielectrophoretic force, and the polystyrene beads are delivered into the upper flow path 3316 (3323) by receiving the negative dielectrophoretic force.

Figure 12:
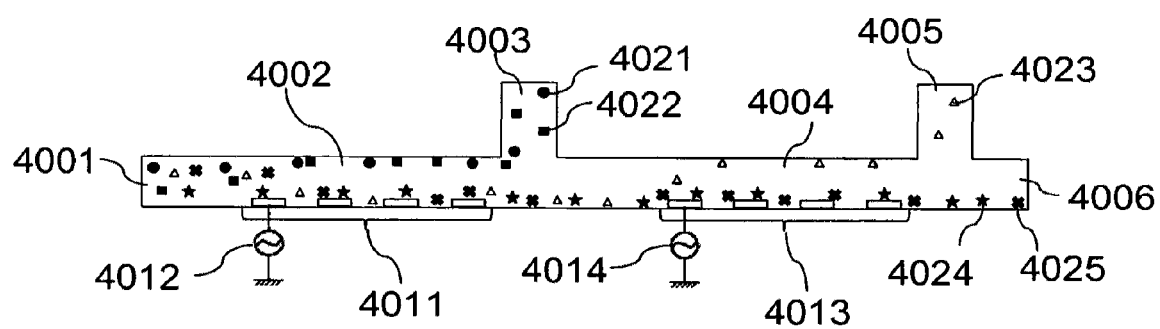
FIG. 12 is a side view schematically showing one example of a device for continuously separating and purifying particulates by difference in frequency responsiveness of polarities of dielectrophoretic forces.

The examples shown in FIGS. 8 to 11 are merely used for explaining the principle of this technique. Practically, by connecting a plurality of units using this technique in line, the dielectrophoretic forces of two or more different frequencies are sequentially applied on samples. Thus, cells which react differently against the dielectrophoretic forces of different frequencies can be picked up and purified more precisely. FIG. 12 is a side view showing one example of a structure of a device for continuously separating particulates into a plurality of types and purifying them by difference in frequency responsiveness of polarities of the dielectrophoretic forces applying the particulates by combining a plurality of separation and purification devices shown in FIG. 8. The device includes a fine flow path arranged two-dimensionally on a planar chip having two three-dimensional branched flow paths, and two pair of thin-film electrodes for applying the dielectrophoretic force. A sample liquid introduced from a sample liquid inlet 4001 is branched into a first particulate outlet 4003 and a second dielectrophoretic force applying portion 4004 after passing through a first dielectrophoretic force applying portion 4002. Then, the sample liquid is branched into a second particulate outlet 4005 and a third particulate outlet 4006 after passing through the second dielectrophoretic force applying portion 4004. In the first dielectrophoretic force applying portion 4002, the particulates in the sample liquid receive the dielectrophoretic force from an AC electric field 4012 of a frequency f1 applying to a first V-shaped interdigitated electrode 4011. Particulates indicated by black circle marks 4021 and black square marks 4022 receive the negative dielectrophoretic force from the AC electric field 4012 of the frequency f1, and thus are collected on the upper surface of the flow path to be picked up from the first particulate outlet 4003. On the other hand, particulates indicated by white triangular marks 4023, black asterisks 4024, and black X marks 4025 receive the positive dielectrophoretic force from the AC electric field 4012 of the frequency f1, and thus are collected on the lower surface of the flow path in the first dielectrophoretic force applying portion 4005 to be delivered into the second dielectrophoretic force applying portion 4004. In the second dielectrophoretic force applying portion 4004, the particulates in the sample liquid receive the dielectrophoretic force from an AC electric field 4014 of a frequency f2 applying to a second V-shaped interdigitated electrode 4013. Since the particulates indicated by the white triangular marks 4023 receive the negative dielectrophoretic force from the AC electric field 4014 of the frequency f2, the particulates are collected on the upper surface of the flow path and picked up from the second particulate outlet 4005. On the other hand, since the particulates indicated by the black asterisks 4024 and black X marks 4025 receive the positive dielectrophoretic force from the AC electric field 4014 of the frequency f2, the particulates are collected on the lower surface of the flow path and picked up from the third particulate outlet 4006. Thus, particulates can be separated and purified from a suspended sample liquid of a plurality of types of particulates by the difference in frequency responsiveness in the polarities of the dielectrophoretic forces.

Figure 13:
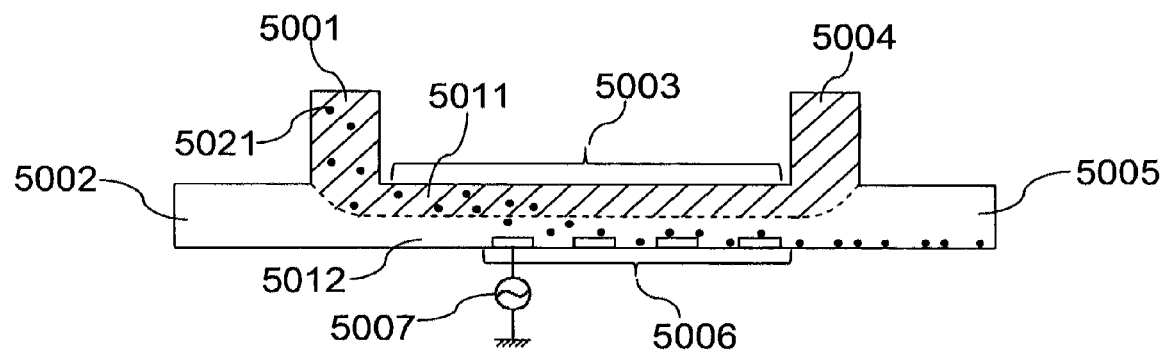
FIG. 13 is a side view schematically showing one example of a device for continuously exchanging a liquid in which particulates are suspended by a dielectrophoretic force.

Also, for example, after a specific media such as stain solution is used, the media can be effectively removed by this technique. FIG. 13 is a side view schematically showing one example of a device for continuously exchanging a solvent in a sample liquid in which particulates are suspended by the dielectrophoretic force. The device includes a series of fine flow paths arranged on a planar chip which comprise two flow paths united on a chip surface in the vertical direction, a flow path including a dielectrophoretic force applying portion, and two flow paths branched in the vertical direction, and a thin-film electrode formed on a bottom surface of the flow path for applying the dielectrophoretic force. A sample liquid introduced from a sample liquid inlet 5001 flows together with an exchange solution introduced from an exchange solution inlet 5002 but does not mix with the exchange solution because the flow path has a fine structure. The sample liquid and the exchange solution are respectively divided into an upper laminar flow 5011 (indicated by slanting lines) and a lower laminar flow 5012 in the vertical direction of the flow path. After passing through a dielectrophoretic force applying portion 5003, the sample liquid and the exchange solution are discharged respectively, without being mixed, through a waste liquid outlet 5004 and a particulate re-suspended solution outlet 5005 which are branched in the vertical direction of the flow path. At this point, the particulates 5021 suspended in the sample liquid is delivered into the dielectrophoretic force applying portion 5003 while flowing through the upper laminar flow 5011. When an AC electric field 5007 of a specific frequency is applied to a V-shaped interdigitated electrode 5006 arranged on a bottom surface of the dielectrophoretic force applying portion 5003, the particulates 5021 flowing in the upper laminar flow 5011 are attracted to a bottom surface side of the flow path by receiving the dielectrophoretic force. Consequently, the particulates 5021 are moved into the lower laminar flow 5012 from the upper laminar flow 5011. By selecting such a frequency that a solute contained in the sample solution does not receive the positive dielectrophoretic force, only the particulates 5021 can be moved into the lower laminar flow 5012 without mixing the solute in the sample solution into the exchange solution. The particulates 5021 moved into the lower laminar flow 5012 can be picked up from the particulate re-suspended solution outlet 5004 and the sample liquid in the upper laminar flow 5011 from which the particulates 5021 are removed is discharged through the waste liquid outlet 5004.

Industrial Applicability

The present invention provides a cell separation system without cross-contamination, and is useful in the field of medicine, especially in the field of regeneration medicine. Also, the present invention is useful as a single-use device for concentrating and separating cells without contamination which does not require pre-treatment such as cell concentration and which can separate the cells stably.

Reference Signs List

1: device for concentrating and separating cells; 10, 201: chip; 20: sample liquid inlet; 30: cell concentration portion; 40, 41: flow path resistance adjustment portion; 50: waste liquid outlet; 51: waste liquid outlet; 60: cell concentrate inlet; 70: cell arrangement portion; 80: cell separation portion; 90: purified cell outlet; 100: sample liquid flow; 101, 102: concentrated cell flow; 204, 218: flow path; 221: cell detection area; 222: cell separation area; 225: light source; 226, 246, 252: filter; 244: objective lens; 245: dichroic mirror; 251: mirror; 247, 253: lens; 248: fluorescence detector; 254: cell imaging camera; 260: information analyzer; 270: cell separation control signal; 1010: sample liquid inlet; 1020: waste liquid outlet; 1050: concentration portion parallel flow path; 1060: concentration portion oblique flow path; 1070: branched flow path for sorting concentrated particulates; 2010: oblique interdigitated electrode for concentration; 2020, 2021: connection point of interdigitated electrode for concentration; 2110: V-shaped interdigitated electrode for convergence; 2120, 2121: connection point of V-shaped interdigitated electrode for convergence; 2130, 2131: electrode; 2210: oblique electrode for selection; 2220, 2221: connection point of oblique electrode for selection; 3001: electrode chip; 3002, 3002': connection point of AC source; 3003: V-shaped interdigitated electrode; 3101: flow path chip; 3102: sample liquid inlet; 3103: upper flow path outlet; 3104: lower flow path outlet; 3105: dielectrophoretic force applying portion; 3106: upper flow path; 3107: lower flow path; 3108: three-dimensional branched portion; 3201: particulate receiving negative dielectrophoretic force; 3202: particulate receiving positive dielectrophoretic force; 3301: lower layer portion of device; 3302: upper layer portion of device; 3311: sample liquid inlet; 3312: dielectrophoretic force applying portion; 3313, 3313': V-shaped interdigitated electrode; 3314: three-dimensional branched portion; 3315: lower flow path; 3316: upper flow path; 3321: collection of Bacillusu subtilis and polystyrene beads at the center of flow path; 3322: flow of Bacillusu subtilis into lower flow path; 3323: flow of polystyrene beads into upper flow path; 4001: sample liquid inlet; 4002: first dielectrophoretic force applying portion; 4003: first particulate outlet; 4004: second dielectrophoretic force applying portion; 4005: second particulate outlet; 4006: third particulate outlet; 4011: first V-shaped interdigitated electrode; 4012: AC electric field of frequency f1; 4013: second V-shaped interdigitated electrode; 4014: AC electric field of frequency f2; 4021, 4022, 4023, 4024, 4025: particulate; 5001: sample liquid inlet; 5002: exchange solution inlet; 5003: dielectrophoretic force applying portion; 5004: waste liquid outlet; 5005: particulate re-suspended solution outlet; 5006: V-shaped interdigitated electrode; 5007: AC electric field; 5011: upper laminar flow; 5012: lower laminar flow; 5021: particulate

The invention claimed is:

1. A cell separation chip, comprising:
   a planar substrate;
   a flow path formed on one side of the planar substrate and configured to allow a sample liquid containing cells to flow down;
   a cell concentration area provided in the flow path and configured to concentrate the cells;
   a cell arrangement area provided in the flow path and configured to arrange the cells; and
   a cell separation area provided in the flow path and configured to separate the cells,
   wherein the cell separation area comprises:
      branched flow paths connected to the downstream end of the flow path, comprising an upper flow path and a lower flow path separated in the vertical direction of the flow path relative to the one surface of the planar substrate,
   wherein
      the flow path is branched downstream of the cell concentration area,
      the sample liquid containing the cells passing through the cell concentration area is delivered into one of the branched flow paths, and
      the cell arrangement area and the cell separation area are provided in the one of the branched flow paths; and
   wherein
      the cell separation area is provided downstream of the cell arrangement area.

2. The cell separation chip according to claim 1, comprising a cell information detection area upstream of the cell separation area in the branched flow path,
   wherein the cells are separated in the cell separation area based on information relating to the cells detected in the cell information detection area.

3. The cell separation chip according to claim 1, wherein the branched flow path is further branched downstream of the cell separation area, and
   the sample liquid containing the cells separated in the cell separation area is delivered into one of the further branched flow paths.

4. The cell separation chip according to claim 1, comprising a mechanism for applying an ultrasonic radiation pressure, a gravitational force, an electrostatic force, or a dielectrophoretic force to the cells in the cell concentration area.

5. The cell separation chip according to claim 4, wherein the mechanism includes an electrode which is disposed on a surface of the flow path in the cell concentration area and generates an electrostatic force or a dielectrophoretic force to the cells.

6. The cell separation chip according to claim 5, wherein the electrode is an interdigitated electrode array.

7. The cell separation chip according to claim 6, wherein the interdigitated electrode array comprises an array of V-shaped electrodes, and a vertex of a V-shape of each V-shaped electrode is oriented toward a downstream of the flow path.

8. The cell separation chip according to claim 1, wherein the cell arrangement area provided in the branched flow path comprises an interdigitated electrode array comprising an array of V-shaped electrodes arranged on one surface of the flow path in the cell arrangement area so that the vertex of the V-shape of each V-shaped electrode is oriented toward the downstream of the branched flow path.

9. The cell separation chip according to claim 1, wherein the flow path is branched downstream of the cell separation area, and the cells separated in a direction away from the electrodes or in a direction approaching the electrodes in the flow path are delivered into each branched flow path.

10. A device for concentrating and separating cells, comprising:
   (a) a cell separation chip including
      (i) a planar substrate,
      (ii) a flow path formed on one surface of the planar substrate and configured to allow a sample liquid containing cells to flow down,
      (iii) a cell concentration area provided in the flow path and configured to concentrate the cells,
      (iv) a cell information detection area provided downstream of the cell concentration area in the flow path and configured to obtain information relating to the cells, and
      (v) a cell separation area provided downstream of the cell information detection area in the flow path and configured to separate the cells, wherein the cell separation area comprises branched flow paths comprising an upper flow path and a lower flow path separated in the vertical direction of the flow path relative to the one surface of the planar substrate;
   (b) a mechanism configured to apply an ultrasonic radiation pressure, a gravitational force, an electrostatic force, or a dielectrophoretic force to the cells in the cell concentration area;
   (c) a cell information detector including an optical system and a cell image processing unit configured to obtain information relating to the cells passing through the cell information detection area; and
   (d) a mechanism configured to apply a voltage to apply an external force to the cells in the cell separation area based on the information relating to the cells obtained by the cell information detector so as to direct the cells into either the upper or the lower branched flow path.

11. The device for concentrating and separating cells according to claim 10, wherein the mechanism described in (b) includes an electrode which is arranged on a surface of the flow path in the cell concentration area and generates dielectrophoretic force.

12. The device for concentrating and separating cells according to claim 11, wherein the electrode is an interdigitated electrode array.

13. The device for concentrating and separating cells according to claim 12, wherein the interdigitated electrode array comprises an array of V-shaped electrodes, and a vertex of a V-shape of each V-shaped electrode is oriented toward a downstream of the flow path.

14. A device for concentrating and separating cells comprising:
   a planar substrate;
   a first flow path provided on one surface of the planar substrate and configured to allow a liquid containing cells to flow down;
   an introduction inlet configured to introduce the liquid into the first flow path;
   a mechanism configured to concentrate the cells flowing down in the first flow path;
   a waste liquid outlet arranged at one end of the first flow path and configured to discharge a waste liquid remaining after the cells are concentrated;
   a second flow path connected to the first flow path and configured to flow the liquid containing the concentrated cells;
   a mechanism provided in the second flow path and configured to arrange the cells in a straight line in the second flow path while flowing the concentrated cells, wherein the mechanism configured to arrange the cells comprises an ultrasonic radiation pressure or a dielectrophoretic force, wherein the dielectrophoretic force is generated by an electrode array having a repeated structure of interdigitated electrodes having an acute end oriented toward a central portion downstream of the second flow path;
   a cell information detector provided downstream of the mechanism in the second flow path and configured to detect a state of each cell in a predetermined area in the second flow path;
   a cell separator provided downstream of the cell information detector in the second flow path and configured to allow the cells to flow down into one of two branched flow paths further downstream of the second flow path in accordance with information relating to the detected cell, wherein the two branched flow paths comprise an upper flow path and a lower flow path separated in the vertical direction of the second flow path relative to the one surface of the planar substrate; and
   two liquid tanks provided downstream of the two branched flow paths and configured to hold a buffer liquid containing the cells flowing through the branched flow paths.

15. The device for concentrating and separating cells according to claim 14, wherein the substrate is a plastic substrate formed by injection molding with a die, and the flow path is formed of a groove formed on one surface of the plastic substrate and a laminate film covering the groove.

16. The device for concentrating and separating cells according to claim 14, wherein the information relating to the cell detected in the cell information detection area is obtained from information relating to an image of the cell.

17. The device for concentrating and separating cells according to claim 14, wherein
   a pair of interdigitated electrodes are provided in the second flow path through which the cells are delivered with a buffer liquid as the cell separating means, and
   the cells are divided into either one of two branched flow paths in the cell separation area depending on whether an alternating current is delivered between the two electrodes or not.

18. The device for concentrating and separating cells according to claim 14, wherein one introduction inlet for introducing the liquid is provided in the first flow path and three or more waste liquid outlets are provided in the first flow path and the second flow path, and a flow path serving as an adjustment portion for adjusting a pressure is added immediately before the three or more waste liquid outlets to equalize a pressure as a drive force for moving the liquid introduced from the introduction inlet at the three or more outlets.

19. A device for concentrating and separating cells, comprising:
   (a) a cell separation chip including
      (i) a planar substrate,
      (ii) a first flow path formed on one surface of the planar substrate and configured to allow a sample liquid containing cells to flow down,
      (iii) a cell concentration area and a cell separation area integrated in the flow path, (iv) an interdigitated electrode array comprising an array of V-shaped electrodes arranged on one surface in the first flow path in the integrated cell concentration area and cell separation area so that a vertex of a V-shape of each V-shaped electrode is oriented toward a downstream of the first flow path, and (v) branched flow paths connected to the downstream end of the first flow path, comprising an upper flow path and a lower flow path separated in the vertical direction of the first flow path relative to the one surface of the planar substrate; and (b) a mechanism configured to apply an AC electric field of a predetermined frequency to apply a dielectrophoretic force of a predetermined frequency depending on the cells to be separated to the interdigitated electrode array.

20. The device for concentrating and purifying cells according to claim 19, wherein the predetermined frequency of the AC electric field is varied.

21. The device for concentrating and separating cells according to claim 19, wherein the flow path for the cell separation chip is branched downstream of the integrated cell concentration area and cell separation area, and the cells separated in a direction away from the electrodes or in a direction approaching the electrodes in the flow path are delivered into each branched flow path.

22. A device for concentrating and separating cells, comprising a plurality of the devices for concentrating and separating cells according to claim 21, wherein at least one of the branched flow paths is connected to an upstream end of a flow path configured to allow the sample liquid containing the cells in another device for concentrating and separating cells to flow down, and the plurality of the devices for concentrating and separating cells are arranged in tandem so that the liquid containing the cells flowing through the at least one of the branched flow paths is further concentrated and separated in the other device for concentrating and separating cells.

* * * * *